United States Patent [19]
Junkel

[11] Patent Number: 6,044,202
[45] Date of Patent: Mar. 28, 2000

[54] HEATED DEODORIZING DEVICE FOR DISPERSING A FRAGRANCE

[75] Inventor: Eric F. Junkel, Des Plaines, Ill.

[73] Assignee: Circulair, Inc., Chicago, Ill.

[21] Appl. No.: 09/276,053

[22] Filed: Mar. 25, 1999

[51] Int. Cl.[7] ............................ A61M 16/00; A24F 25/00; B05B 1/24
[52] U.S. Cl. .............................. 392/390; 239/56; 239/135
[58] Field of Search ...................... 392/386, 390, 392/391, 392, 393, 394, 395; 239/44, 45, 55, 56, 57, 135, 136, 34

[56] References Cited

U.S. PATENT DOCUMENTS

| | | |
|---|---|---|
| D. 315,789 | 3/1991 | Muderlak . |
| 3,288,556 | 11/1966 | Wever, III ............................. 392/390 |
| 4,515,909 | 5/1985 | Sawano et al. . |
| 4,798,935 | 1/1989 | Pezaris .................................. 392/390 |
| 4,804,821 | 2/1989 | Glucksman ............................. 392/390 |
| 4,808,347 | 2/1989 | Dawn . |
| 4,853,517 | 8/1989 | Bowen et al. ......................... 392/390 |
| 4,937,431 | 6/1990 | Jameson et al. . |
| 5,019,434 | 5/1991 | Matsumoto . |
| 5,109,029 | 4/1992 | Malone . |
| 5,175,791 | 12/1992 | Muderlak et al. ..................... 392/390 |
| 5,342,584 | 8/1994 | Fritz et al. . |
| 5,359,801 | 11/1994 | Mattucci et al. . |
| 5,392,379 | 2/1995 | Fussell . |
| 5,522,008 | 5/1996 | Bernard . |
| 5,547,636 | 8/1996 | Vick et al. . |
| 5,556,030 | 9/1996 | Paul . |
| 5,556,192 | 9/1996 | Wang . |
| 5,569,511 | 10/1996 | Spector . |
| 5,647,052 | 7/1997 | Patel et al. ............................. 392/390 |
| 5,662,835 | 9/1997 | Collingwood . |
| 5,667,732 | 9/1997 | Lederer . |
| 5,690,720 | 11/1997 | Spero . |
| 5,695,692 | 12/1997 | Kennedy . |
| 5,744,106 | 4/1998 | Eagle . |
| 5,782,409 | 7/1998 | Paul . |

*Primary Examiner*—Sang Paik
*Attorney, Agent, or Firm*—Gifford, Krass, Groh, Sprinkle, Anderson & Citkowski, P.C.

[57] ABSTRACT

A deodorizing device for diffusing and dispersing a volume of a desired fragrant compound intermixed with a body constructed of a plasticized resinous material. The fragrant compound forms a front enclosure of the body which is both structural and/or decorative in nature. A plurality of individual and heat generating resistors are connected in series and formed integrally with a rear enclosure of the device. A pair of alternating current (AC) attachment blades extend from the rear of the device and are operably engaged with the resistors via a thermistor to achieve a desired level of diffusion of the fragrant compounds. The construction of the body and fragrant compound is such that the compound is diffused at a decreasing rate until expended. The fragrant compound is in the preferred embodiment a releasably and replaceably securable resinous element which is impregnated with the fragrant compound.

16 Claims, 5 Drawing Sheets

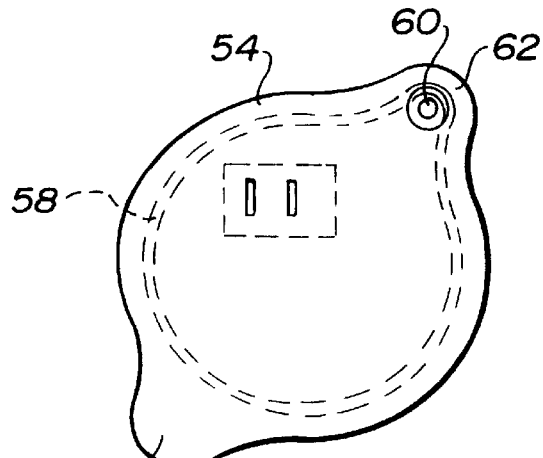
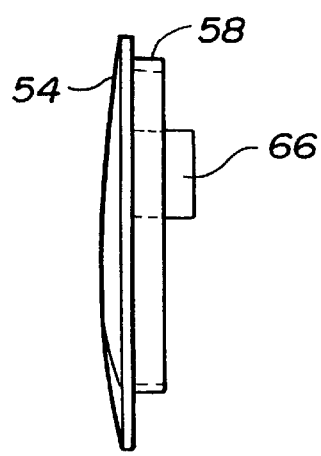
Fig-5
Fig-6
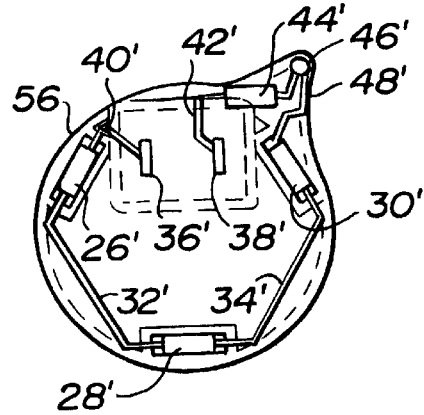
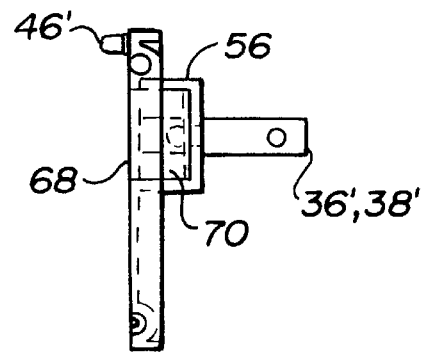
Fig-7
Fig-8
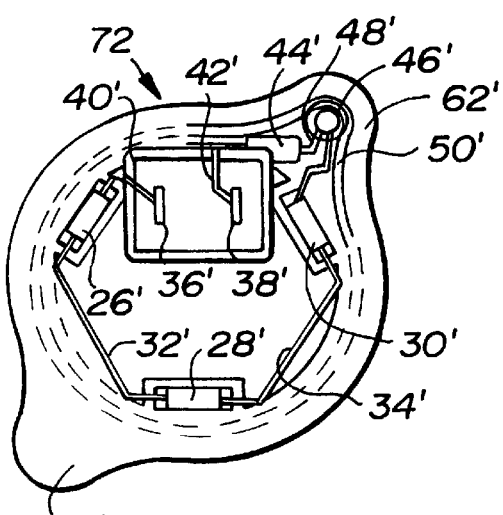
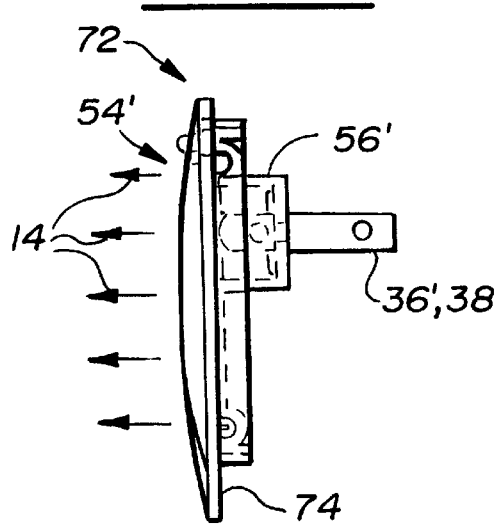
Fig-9
Fig-10

HEATED DEODORIZING DEVICE FOR DISPERSING A FRAGRANCE

BACKGROUND OF THE INVENTION

1. Field of the Invention

The present invention relates generally to scenting and fragrancing devices and, more particularly, to an improved heated deodorizing device for generating and dispersing a desired scent or fragrance and distributing the scent to a surrounding environment.

2. Description of the Prior Art

Fragrant compounds are well known in the art for masking foul odors with more pleasing scents or odors which are introduced into enclosed areas by the release of natural and/or synthetic compounds. The medical art of aromatherapy administers by inhalation, ingestion or skin absorption small amounts of the essential oils of plants that are believed to possess therapeutic properties. Also, fragrant compounds may be added to the construction materials of products that are used in odiferous environments in an attempt to mask unpleasant odors.

One form of known deodorizing device involves evaporation of a solid or liquid containing a fragrance compound and which is evaporated through the application of heat or the opening of a vent between a chamber within a body containing the fragrant compound and the surrounding enclosed area. Other known prior art examples introduce the fragrant aroma into the surrounding environment by atomization of a liquid fragrance compound or by blowing air past a reservoir of a liquid or solid material containing the fragrant compound.

U.S. Pat. No. 5,522,008, issued to Bernard, discloses a vaporizing device having a heating unit with a pair of electrical connector terminals staked to a substantially rigid substrate having a serpentine resistance type heating element printed thereon and electrically connected to the terminals. An insulating conformal layer coats the heating element, wicking into the interstices of the region between the electrical terminals and the openings in the substrate receiving the terminals to significantly enhance the structural strength of the device.

U.S. Pat. No. 5,556,192, issued to Wang, discloses a perfumer structure having an optically controlled night light. The perfumer structure includes a heat conductor element wrapped by a heat conductive and fireproof plastic material, such as provided by a body securable to an AC power outlet, for generating heat to vaporize a solid perfume insert and to disperse a perfume gas.

A major drawback of such prior art devices includes the incidence of leakage of liquid based compounds during manufacture, storage and/or use of such devices. Also, the cost of constructing reservoirs in the fragrancing/deodorizing devices adds to the cost and complexity of such devices and the prior art further suffers from the inability to provide the fragrancing compounds in a measured and continuous fashion so as to achieve optimal efficiency of the devices. Furthermore, the construction of existing plug-in deodorizers with fragrancing inserts suffer from the shortcoming of having fairly small effective areas of fragrancing. Furthermore, may deodorizers are not especially decorative and do not give a hint as to the nature of the fragrance they contain.

SUMMARY OF THE PRESENT INVENTION

The present invention is a deodorizing device which is an improvement over the prior art in that it provides for measured and continuous dispersal of a fragrant compound into a surrounding environmental area. The device includes a body constructed of a plasticized resin material and containing a volume of a volatile liquid fragrant compound which is mixed with the resin material forms both structural and decorative aspects of the body. A plurality of individual electrically powered and heat generating resistor elements are integrally formed within the body and are connected to a pair of AC attachment blades via a rectifying diode. The diode is only used when an LED is the type of indicator lamp. Incandescent or neon lamps may also be used in the application, however they do not require a diode. The diode blocks a reverse high voltage when driving with an AC source, which would otherwise damage the LED. The heat generated by the individual and interconnected resistor elements is transferred to the portion of the resin body containing the volume of the fragrant compound, whereby the fragrant compound is caused to diffuse to a surface of the body and to evaporate into the air of the surrounding environs.

In a first preferred embodiment, the fragrant compound is limited to an integral front enclosure of the body and the resistors, rectifier and AC blades are integrally formed within a rear enclosure to which the front enclosure is fixedly secured. In a further embodiment, the body further includes a barrier which is interposed between the front enclosure and the rear enclosure and for the purpose of insulating/electrically isolating the heat generating and resistive components from the front enclosure and to retard the degree of heat transfer and diffusion which would otherwise occur across the front enclosure.

The front enclosure including the fragrant compound may further be provided as a releasable element which is frictionally attachable to said body and which permits like shaped replacement elements to be releasably secured and so as to extend the life of the device. It is further desired to provide the releasable element with at least one gripping tab to facilitate removal and replacement and it is also desired to select an overall shape of the front enclosure to correspond with one of a group of synthetic fragrant compounds, such as a lemon shape to coincide with a lemon scent. The consistent advantage of the present invention in each of the above recited embodiments is that the fragrant compound is dispensed in a measured and decreasing rate until expended and so as to provide the optimal efficiency of fragrance dispersal.

In further preferred embodiments, the established temperature of the resistor elements can be kept within a specified range through the use of a thermistor or a positive temperature coefficient-type resistance heating element, such elements typically replacing one of the plurality of series-connected resistors. An LED (light emitting diode) may also be connected in series to the rectifier diode and the resistors and functions in one aspect to indicate an on/off status of the device. In a further embodiment, the LED is provided with sufficient power to function as a night light. Additionally, a base structure can be incorporated into the deodorizing device which creates a lowered or step-down voltage for establishing more controlled diffusion of the scenting compound and for preventing or at least slowing a dielectric breakdown of the plastic within which the fragrancing compound is embedded. A further variation is illustrated of a screw-in deodorizer attachment which includes an externally threaded Edison shaped base and which is capable of being rotatably engaged within a conventional light socket.

BRIEF DESCRIPTION OF THE DRAWINGS

Reference will now be made to the attached drawings, when read in combination with the following specification, wherein like reference numerals refer to like parts throughout the several views, and in which:

FIG. 5 is a view of the front enclosure according to the embodiment of FIG. 3;

FIG. 6 is a corresponding side view of the front enclosure as shown in FIG. 5;

FIG. 7 is a view of the rear enclosure revealing the electrical heat generating circuitry according to the embodiment of FIG. 3;

FIG. 8 is a side view of the rear enclosure as shown in FIG. 7;

FIG. 9 is a view illustrating a further preferred embodiment of the present invention in which the front enclosure containing the fragrant compound is capable of releasably and replaceably secured to the body;

FIG. 10 is a side view of the further embodiment illustrated in FIG. 9;

DETAILED DESCRIPTION OF THE PREFERRED EMBODIMENTS

Figure 1:
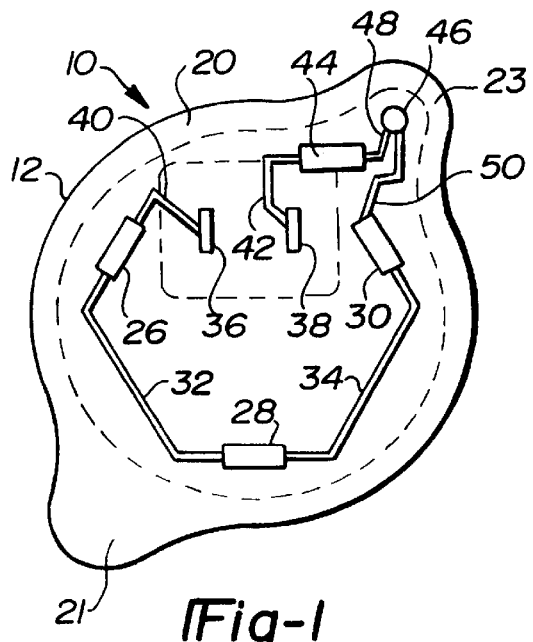
FIG. 1 is a heat activated deodorizing device for dispersing a desired fragrance in a first preferred embodiment and illustrating in exposed fashion the electrical heat generating components according to the present invention.
Figure 2:
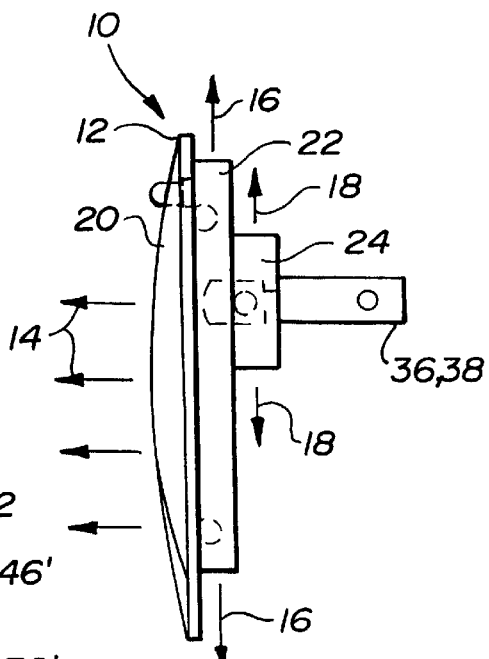
FIG. 2 is a side view of deodorizing device according to the preferred embodiment of FIG. 1 and illustrating the issuance of the fragrance in a vapor form from the surface of the body for evaporation within the surrounding air.

Referring now to FIGS. 1 and 2, a deodorizing device for issuing a desired fragrance is illustrated at 10 according to a first preferred embodiment of the present invention and includes a body 12 constructed of a plasticized resin. According to the present invention, both structural and/or decorative portions of the plasticized resin body are preformed with a volatile liquid mixture of a specified fragrancing compound and are constructed by such known processes as injection molding and the like. In the first preferred embodiment of FIGS. 1 and 2, substantially the entire resin structure of the body 12 is formed of mixed fragrancing compound and so that the fragrance compound is diffused to selected surface locations along the body 12 and issued therefrom as a vapor, as indicated by frontal directional arrows 14 and lateral directional arrows 16 and 18 for evaporation within the air of the surrounding environs.

As is best shown in the side view of FIG. 2, the body 12 includes a front 20, a midsection 22 and a rear 24 which are all formed as one integral piece. The outer periphery of the front 20 in FIG. 1 further references shaped outer portions 21 and 23 which provide the front 20 with a substantially lemon shaped appearance and it is desired in one preferred embodiment to provide a synthetically created lemon scenting to the fragrancing compound to coincide with this shape.

The drawing illustration of FIG. 1 reveals an electrical circuit arrangement for generating heat within the body 12 and to effectuate a desired level of diffusion and radiation of the fragrant compounds intermixed with the plasticized resin of the body. Specifically, a plurality of electrical resistor elements 26, 28 and 30 are established at spaced apart locations around a circumference of the body 12 and are interconnected in series by electrical line 32 (connecting resistor elements 26 and 28) and electrical line 34 (connecting resistor elements 28 and 30). The resistors are preferably arrayed such that the volume of resin is heated as evenly as possible. Furthermore, the provision of three resistors may be substituted by a single resistor, two resistors or any other plurality as is desired and as dictated by the size and thickness of the resin body.

A pair of AC (alternating current) attachment blades extend from the rear section 24 of the body 12 and are capable of being operatively engaged with an AC power outlet to supply the electrically powered resistor elements 26, 28 and 30. A first lead 40 extends from a selected blade (see 36) to the first resistor 26 and a further lead 42 extends from the other AC blade 38 to a rectifier diode 44 for providing half wave rectification of an alternating wave current provided through the power source to pulsed DC current for supply to the operating circuitry. It is further understood that the present device is not limited to AC sources. A direct current (DC) source could be used with suitably designated attachment blades and power conditioning. It is also envisioned that a low voltage plug-in power supply could have a receptacle which would accept the deodorizer, except that some other sort of blade shape would be required to prevent insertion of incompatible devices. The attachment means could also consist of a miniature Edison base lamp which could be screwed into a string of Christmas tree lights. The deodorizer in this instance would include the fragrance of Christmas trees or apple/cinnamon or other seasonal fragrances.

A light emitting diode (L.E.D.) 46 is operatively connected to the rectifier diode 44 via a line 48 extending therebetween and a further line 50 interconnects the L.E.D. 46 and third resistor element 30 to establish a closed series circuit between the AC power supply, diode 44, L.E.D 46 and resistors 26, 28, and 30. The L.E.D. is typically utilized only and is the type of indicator lamp employed. Incandescent or neon lamps could also be used in the application, but do not require the diode. The diode functions to block the reverse high voltage when driving with an AC source, which would otherwise burn out the L.E.D.

Figure 3:
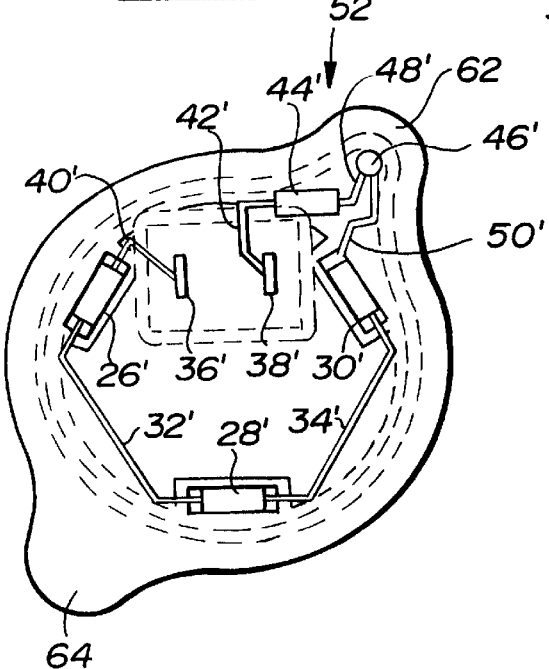
FIG. 3 is a view similar to that shown in FIG. 1 and further illustrating a further preferred embodiment in which a front enclosure containing the fragrant compound is molded around a separate rear enclosure.
Figure 4:
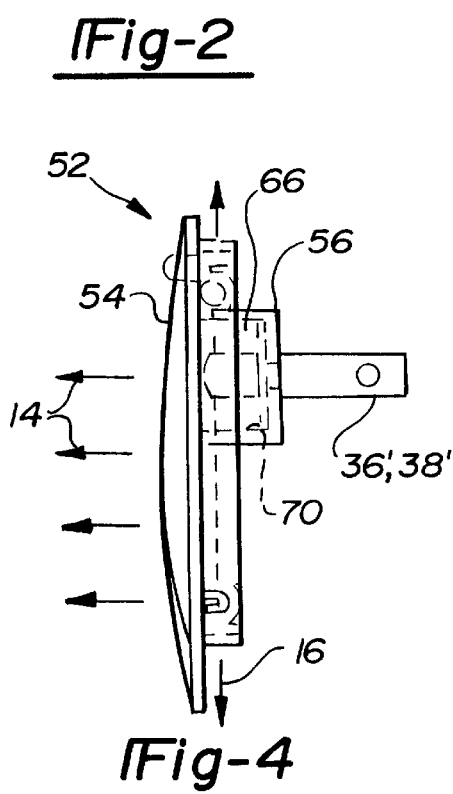
FIG. 4 is a side view of the deodorizing device according to the preferred embodiment of FIG. 3 and once again illustrating the nature of the issuance of fragrance from selected surfaces of the body for evaporation within the surrounding air.

A further preferred embodiment 52 of a deodorizing device is illustrated in FIGS. 3 and 4 and is similar in most respects to that illustrated at 10 in FIGS. 1 and 2, with the exception that a front enclosure 54 of the device body is manufactured as a first separate member containing the fragrancing compound and a corresponding rear enclosure 56 is manufactured as a second element containing the electrical/heat generating circuitry. The rear enclosure 56 is subsequently molded together with the front enclosure 54 and the advantage of the second preferred embodiment 52 allows self-fixtured preassembly of the electrical elements within the rear enclosure 56 and further permits the choice of a rear enclosure material exhibiting better electrical and flame-resistant properties as opposed to the plasticized resin material of the front enclosure 54. The embodiments disclosed herein do not necessarily require that overmolding of the front enclosure upon the rear enclosure, however it is understood that it is a superior solution from a manufacturing point of view.

Referring to FIG. 3, the electrical circuitry of the second preferred embodiment 52 is largely identical to that illustrated in the first embodiment 10 and includes the provision of first 26', second 28' and third 30' electrical resistor elements, interconnecting lines 32' and 34', AC attachment blades 36' and 38', rectifier diode 44', L.E.D. 46' and leads 42', 48' and 50' for completing a closed circuit.

Specifically, referring further to FIGS. 5–8, front and side views are illustrated of both the front enclosure 54 and rear enclosure 56 and illustrate with greater detail the molding attachment of the two pieces together. The front enclosure 54 illustrated in FIG. 5 further references in phantom at 56, as well as in solid in the side view of FIG. 6, a rearwardly extending and annular shaped connecting portion 58. Also included with the front enclosure 54 is an aperture 60 (for seating the L.E.D. 46'), shaped outer portions 62 and 64 and a further rearwardly extending connecting portion 66 extending from the front enclosure 54. Referring further to FIGS. 7 and 8, and particularly the side view of FIG. 8, the rear enclosure 56 includes a substantially flat and annular cross sectionally shaped surface 68 which seats within an open interior defined by the annular shaped and rearwardly extending portion 58. A further rearward portion 70 defining a recess extends from the surface 68 of the rear enclosure 56 and seats the further connecting portion 66 of the front enclosure 54 to complete the assembly of the device 52.

Referring now to FIGS. 9 and 10, a further preferred embodiment is shown at 72 of a deodorizing device according to the present invention in which a barrier member 74 is secured to a rear enclosure 56' either by molding or other mechanical attachment means. FIG. 9 in particular may also be viewed as illustrating the front enclosure being overmolded onto the rear enclosure.

A front enclosure 54' is then releasably securable to the barrier member 74 the barrier member provides the function of electrically isolating the circuitry contained within the rear enclosure 56' (identically as described in the previous preferred embodiment of FIGS. 3–8) and so as to prevent the material of the front enclosure 54' from melting and/or the fragrant compound contained within the resin structure of the front enclosure 54' from being prematurely discharged. The barrier member 74 is constructed of a suitable resinous material which provides the necessary electrical insulation of the components contained within the rear enclosure 56' while at the same time permitting the desired level of heat transfer across the boundary of the barrier member 74 and to the fragrant compounds contained within the front enclosure 54'.

Figure 11:
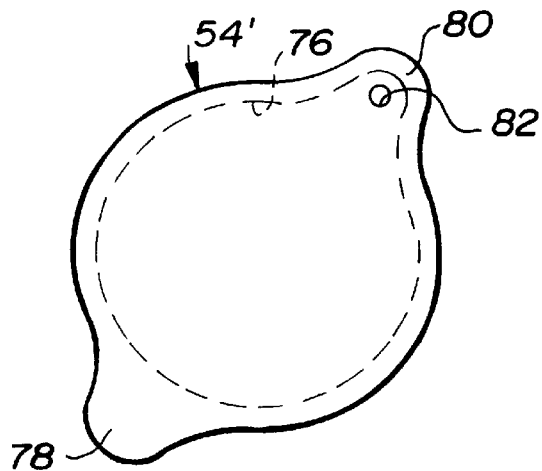
FIG. 11 is a view of the removable/replaceable front enclosure according to the embodiment of FIG. 9.
Figure 12:
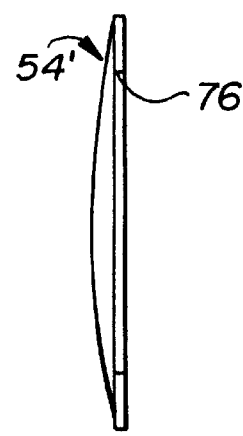
FIG. 12 is a side view of the front enclosure as shown in FIG. 11.
Figure 13:
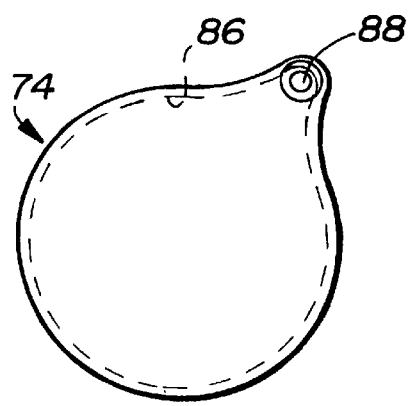
FIG. 13 is a view of a barrier interposed between the front enclosure and rear enclosure for electrically isolating the elements contained within the rear enclosure member.
Figure 14:
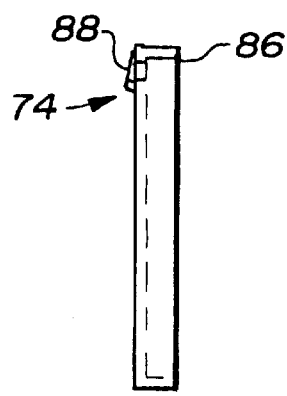
FIG. 14 is a side view of the barrier as shown in FIG. 13.
Figure 15:
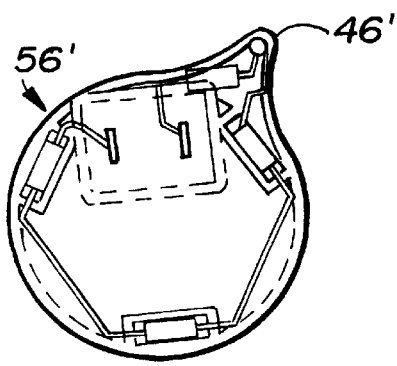
FIG. 15 is a view of the rear enclosure revealing the electrical heat generating circuitry according to the embodiment of FIG. 9.
Figure 16:
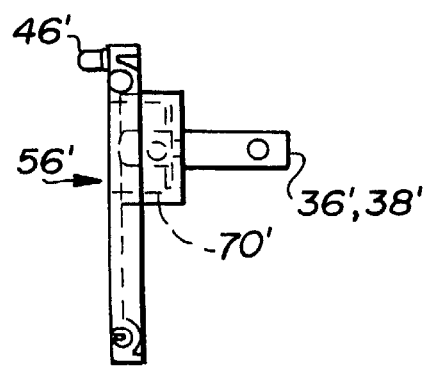
FIG. 16 is a side view of the rear enclosure as shown in FIG. 15.

Referring further to FIGS. 11–16, corresponding frontal and side views are illustrated of the front enclosure 54', barrier member 74 and rear enclosure 56' according to the further preferred embodiment 72 of the present invention. Specifically, FIGS. 11 and 12 illustrate the configuration of the front enclosure 54' which include a decorative outer configuration on a front face and an inwardly facing annular rim 76 located within a rear face (see phantom lines of FIG. 11 and solid line in FIG. 12 side view) and defining a rear facing recess. Shaped outer portions 78 and 80 are again referenced which are similarly shaped to the corresponding front enclosures of the earlier preferred embodiments and the purpose of the outer portions 78 and 80 are to both function as gripping tabs to facilitate disengagement of the front enclosure 54' from the remainder of the body (barrier member and rear enclosure) as well as to provide the front enclosure 54' with an overall lemon shaped appearance which corresponds nicely to a synthetic impregnated scenting means provided to the front enclosure 54'. An aperture 82 is again provided for seating the L.E.D. element 46' as in earlier embodiments.

Figure 19:
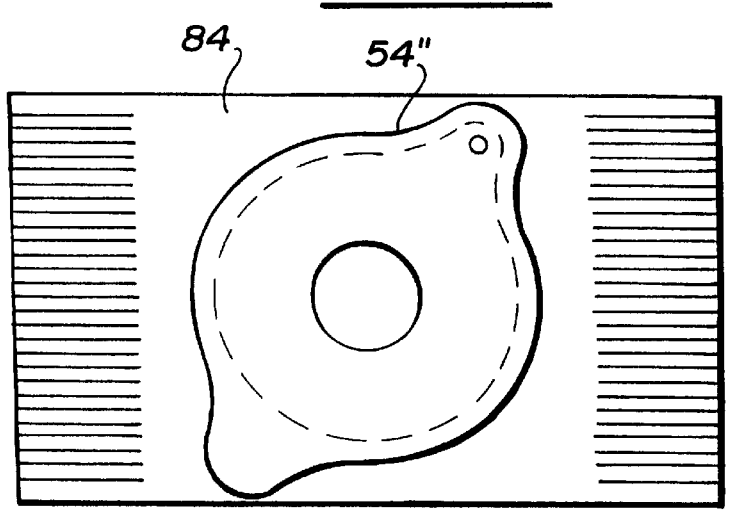
FIG. 19 is a view of a packaged fragrant element which is capable of being replaceably secured to the body of the device such as is illustrated in FIG. 9 according to the present invention.
Figure 20:
FIG. 20 is a side view of the packaged fragrant element illustrated in FIG. 19.

Referring further to FIGS. 19 and 20, the scented front enclosure is illustrated as a replacement element 54" sealed within an air tight package 84. While illustrated as an identically shaped element to that shown in all of the preferred embodiments throughout the instant disclosure, i.e., lemon shaped, it is understood that a wide variety of alternately shaped replacement elements may also be provided and each scented according to its visual appearance. Examples of such shapes may include cherries, oranges, watermelons, lemons or any other fruit or other shaped articles such as pine scented and tree shaped diffusers to which a definitive scent may be associated.

Referring back to FIGS. 13 and 14, the barrier member 74 is again illustrated and includes an outer shape consistent with that of the front enclosure 54' and is suitable for being resistively engaged within the recessed area defined by the inwardly facing annular rim 76 so as to resecurably mount the front enclosure 54' to the barrier member 74. The barrier member 74 further includes its own rearwardly extending annular rim 86 which defines a rear facing recess and a further apertured portions 88 which aligns with the corresponding portion 82 in the front enclosure 54' for permitting visual inspection of the L.E.D. 46' of the rear enclosure 56'.

Referring again to FIGS. 15 and 16, the rear enclosure 56' is again shown in front and side view and includes each and every of the features previously referenced in FIGS. 4 and 8 and the generic electrical schematic of FIG. 1, therefore a repeat of all the circuit component elements is not made for purposes of convenience and ease of presentation. The rear enclosure 56' is then molded or mechanically secured to the barrier member 74 so that the rear enclosure 56' fits within the rear facing recess of the member 74 defined within the annular rim 86.

Figure 17:
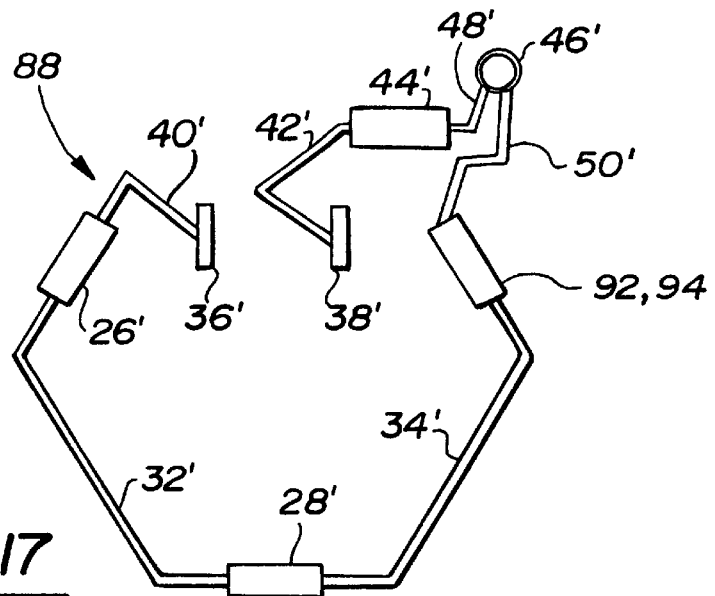
FIG. 17 is an enlarged sectional view illustrating the electrical heat generating components of the rear enclosure according to the present invention.
Figure 18:
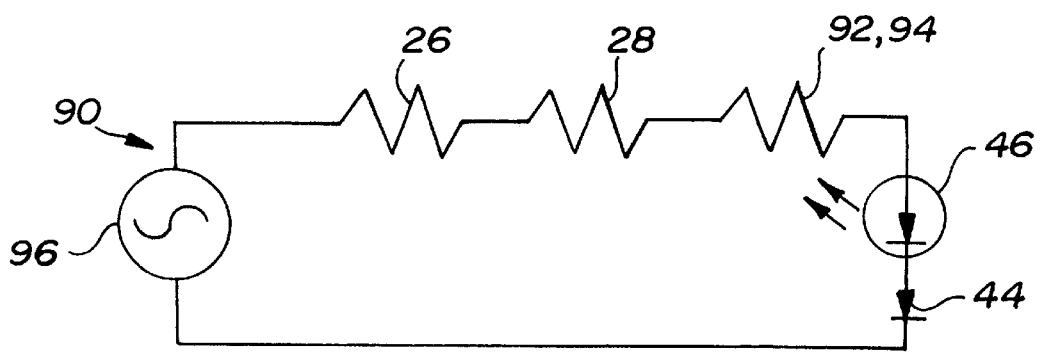
FIG. 18 is an electrical schematic of the components illustrated in the enlarged sectional view of FIG. 17.

Referring finally to FIGS. 17 and 18, additional diagrammatic 88 and schematic 90 illustrations are shown, respectively, of the electrical heat generating components of the present invention. Referring first to the diagram 88 of FIG. 17, the electrical components of the present invention are presented as fairly shown in each of the previous embodiments and include the resistors 26' and 28', AC attachment blades 36' and 38', rectifier diode 44' and L.E.D. display 46'. It is in some instances desirable to establish a fixed temperature range across the resistors and this is accomplished in one manner by replacing a selected resistor (in this case resistor 30') with a thermistor 92. The thermistor 92 functions to cause an increase in electrical resistance upon sensing an increase in temperature, thus causing a drop in current and power which in turn lowers temperature issued by resistors 26 and 28 to operate in like fashion. Alternatively, the thermistor 92 can be replaced by a positive temperature coefficient-type resistance heating element 94 which establishes another known way of fixing a desired temperature or temperature range.

Referring further to FIG. 18, schematic illustrations are provided for the elements described in FIG. 17, these including the standard resistors 26 and 28, thermistor 92 or coefficient type element 94 replacing the third resistor, and rectifier 44 and L.E.D. display 46 as concurrently illustrated in FIG. 17. The L.E.D. display can also function, additional to indicating an on/off status of the device, as a night light if provided with sufficient illumination. Multiple L.E.D.'s or other lamps can be also used to increase power output.

Figure 21:
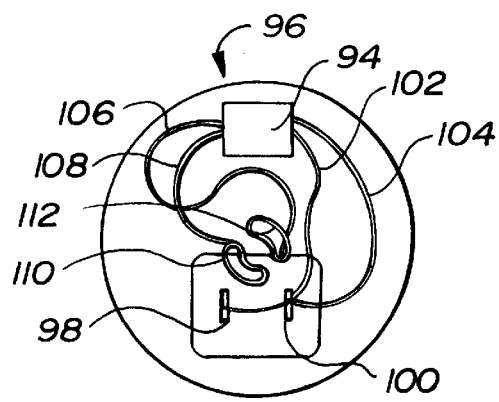
FIG. 21 is a view of a lower voltage converter for use with a further preferred embodiment of the deodorizing device according to the present invention.
Figure 22:
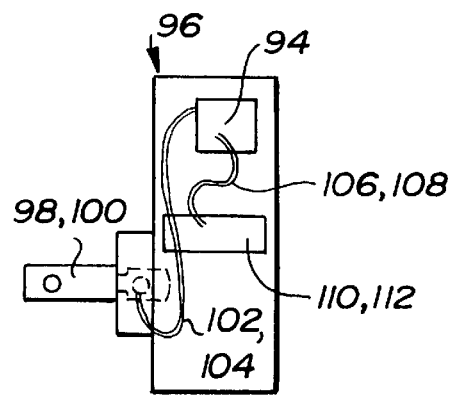
FIG. 22 is a side view of a base portion of a device according to the further preferred embodiment of FIG. 21 and utilizing the voltage conversion device.

Referring now to FIGS. 21–24, a further preferred embodiment of a deodorizer device is illustrated which incorporates a lower voltage supply running through the heating element for preventing or at least slowing down a dielectric breakdown of a resin impregnated plastic containing the fragrancing compound. Referring specifically to FIGS. 21 and 22, a voltage converter element 94 is contained within a base structure 96 and incorporates conventional electrical technology for converting a voltage from a first higher input value to a second lower output value. A pair of AC blades is shown at 98 and 100 and first lead lines 102 and 104 extends from the blades to the low voltage converter. Second lead lines 106 and 108 extends from the low voltage converter 94 to receptacles 110 and 112 substantially centrally located within the base structure 96.

Figures 23, 24:
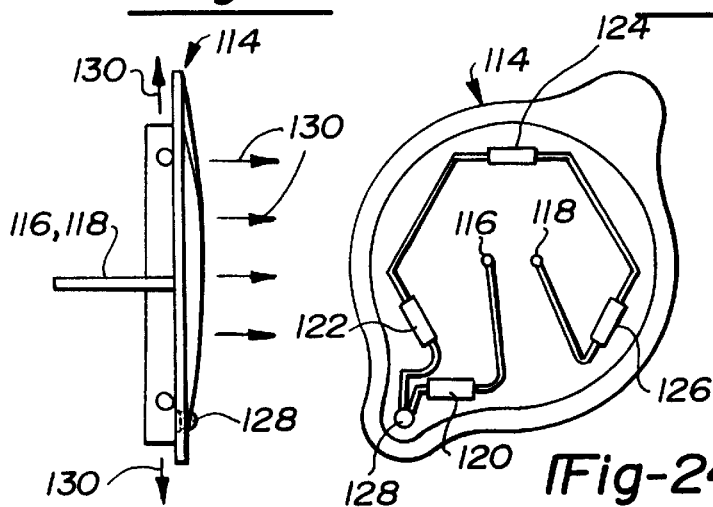
FIG. 23 is a side view of a deodorizer attachment with attachment pins for securing to the base portion of FIG. 22 according to the present invention.
FIG. 24 is a schematic illustrating the further preferred embodiment of FIGS. 21–23 of the present invention.

Referring further to FIGS. 23 and 24, a resin based deodorizing covering element 114 is shown within which is impregnated the desired scenting compound and which includes first and second attachment pins 116 and 118 which extend from a rear surface of the element 114 and are frictionally engaged within the receptacles 110 and 112. As is best shown in the front view of FIG. 24, the covering element 114 includes a fuse 120, diode 122, first resistor heating element 124 and second resistor heating element 126 all interconnected to the pins 116 and 118. An L.E.D. 128 also illuminates to indicate operation of the unit. The functioning of the deodorizing device incorporating the voltage converter/step down element provides for a desired measure of diffusion of the scented compound as illustrated by lines 130.

Figure 25:
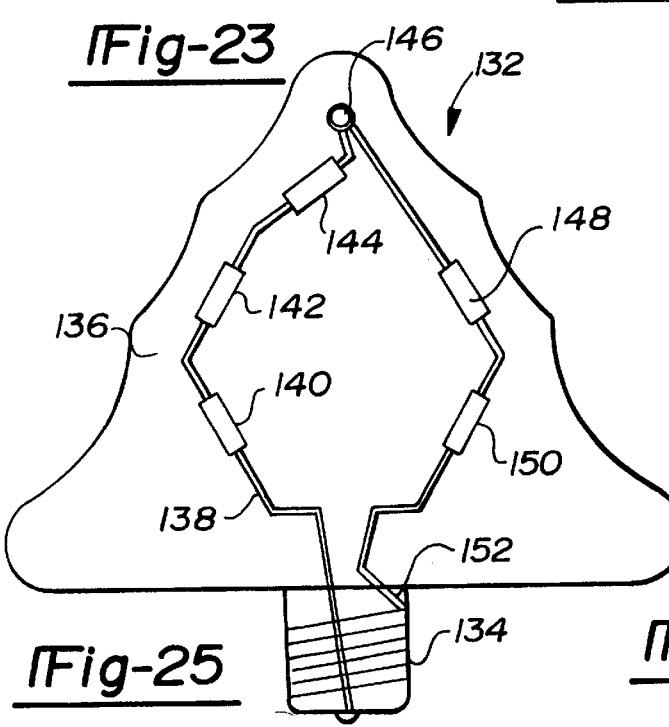
FIG. 25 is a view of a deodorizer according to a further preferred embodiment which is capable of being screwed into a light socket.
Figure 26:
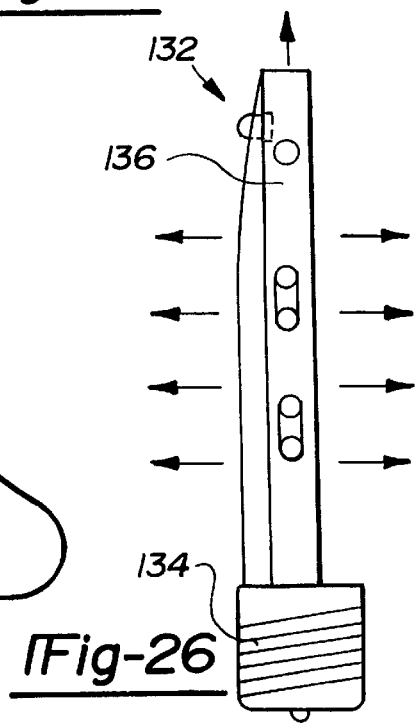
FIG. 26 is a side view of the deodorizer as shown in FIG. 25 illustrating the diffusion of the fragrant deodorizing compound.

Referring finally to FIGS. 25 and 26, an Edison-type deodorizing device is shown at 132 and includes a lamp base 134 which is suitable for engaging within a conventional light socket and which connects to an integral resin impregnated deodorizing body 136. A looping and interconnecting wire 138 extends from the lamp base 134 to heating resistors 140 and 142, to a diode 144, an L.E.D. indicator 146, to additional resistors 148 and 150 and, finally, to terminate at an appropriate ground location in proximity to the lamp base 134.

With a smaller Edison base, the deodorizer could be attached to a string of Christmas lights or installed onto a night light fixture. The device can be improved by including one or more L.E.D. elements to serve as ON/OFF indicators, as a night light or to simulate Christmas tree lights. The device can also be further improved by the addition of the female receptacle for the Edison base of the same size which would allow the deodorizer to be interposed between a lamp and a lamp base (not depicted). Other configurations will become evident to those skilled in the art which will work with rectangular plastic receptacles on strings of miniature lights.

Having described my invention, it will become apparent that the present invention discloses an improved deodorizing device for dispersing a fragrant compound for use in numerous conventional household, as well as aroma therapeutic, applications. Additional preferred embodiments will become apparent to those skilled in the art to which it pertains without deviating from the scope of the appended claims:

I claim:

1. A deodorizing device for dispersing a fragrance, comprising:

a body constructed of a plasticized resin material and having a front side and a spaced apart rear side defining a selected thickness;

a volume of a desired fragrant compound being mixed with said plasticized resin material of said body and forming both structural and decorative elements of said body, said fragrant compound capable of being diffused to selected surface locations of said body;

at least electrically powered heat generating element integrally formed with said body and in proximity to said fragrant compound, said heat generating element operable to facilitate evaporation of said diffused fragrant compounds to an environment surrounding said body;

electrical power input means extending from said body and capable of being operably engaged with an AC power outlet to supply said electrically powered heat generating element; and dispensing means for diffusing said fragrant compound at a decreasing rate until said compound is expended.

2. The deodorizing device according to claim 1, said fragrant compound forming an integral front enclosure of said body which is permanently secured to said heat generating element and said electrical power input means further comprising AC attachment blades extending from said rear side of said body and forming a rear enclosure of said body.

3. The deodorizing device according to claim 2, said body further comprising a barrier interposed between said front enclosure and said rear enclosure of said body for isolating said electrically supplied heat generating elements from said fragrant compound.

4. The deodorizing device according to claim 1, said fragrant compound forming a front enclosure of said body and said heat generating element and AC attachment blades forming a rear enclosure of said body, said body further including a barrier interposed between said front enclosure and said rear enclosure, said front enclosure capable of being releasably and replaceably secured to said body.

5. The deodorizing device according to claim 4, said front enclosure including at least one gripping tab for facilitating removal of said front enclosure from said body.

6. The deodorizing device according to claim 5, said fragrant compound forming said front enclosure further being selected from one of a group of synthetically formed fragrant compounds corresponding to an established fruit shape.

7. The deodorizing device according to claim 6, said front enclosure further comprising an overall configuration selected from a group of shapes consisting of a lemon, a pine tree, a watermelon, an orange, and an apple.

8. The deodorizing device according to claim 1, further comprising a plurality of individual heat generating resistors connected in series for rectifying an alternative wave current into a steady state current for supply to said plurality of resistors.

9. The deodorizing device according to claim 8, further comprising a thermistor connected in series to said plurality of individual heat generating resistors, said thermistor establishing a fixed temperature range for effecting a desired rate of diffusion of said fragrant compounds.

10. The deodorizing device according to claim 8, further comprising an on/off indicator lamp arrayed upon a visible portion of said body and connecting in series with a rectifier diode.

11. The deodorizing device according to claim 10, said indicator lamp further comprising at least one light emitting diode of sufficient intensity to function as a night light lamp.

12. The deodorizing device according to claim 8, further comprising a positive temperature coefficient-type resistance heating element, said coefficient-type resistance heating element establishing a fixed temperature range for effecting a desired rate of diffusion of said fragrant compounds.

13. The deodorizing device according to claim 1, further comprising a voltage converter for stepping down said electrical power input means to effectuate a controlled rate of diffusion of said fragrant compound.

14. The deodorizing device according to claim 13, said device further comprising a base structure within which said voltage converter is incorporated, a pair of AC blades extending from a rearward face of said base structure and in electrical communication with said voltage converter, said base structure further including a pair of receptacles formed within a forward face thereof.

15. The deodorizing device according to claim 14, further comprising a resin based deodorizing covering element having first and second rearwardly extending attachment pins which frictionally engage within said base structure receptacles, said pins conduct said voltage power to said electrically powered heat generating elements integrally formed within said covering element.

16. The deodorizing device according to claim 1, said body further comprising a lamp base capable of being rotatably engaged within a conventional lamp socket.

* * * * *